US00PP37728P2

(12) United States Plant Patent
Kievit

(10) Patent No.: US PP37,728 P2
(45) Date of Patent: Oct. 6, 2026

(54) ***PHLOX* PLANT NAMED 'Balcloudlue'**

(50) Latin Name: *Phlox hybrida*
Varietal Denomination: Balcloudlue

(71) Applicant: Christa Kievit, Vessem (NL)

(72) Inventor: Christa Kievit, Vessem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/285,726

(22) Filed: Jul. 30, 2025

(51) Int. Cl.
*A01H 6/70* (2018.01)
*A01H 5/02* (2018.01)

(52) U.S. Cl.
USPC ..... Plt./320

(58) Field of Classification Search
USPC ..... Plt./320
CPC ..... A01H 6/70; A01H 5/02
See application file for complete search history.

*Primary Examiner* — Keith O. Robinson
(74) *Attorney, Agent, or Firm* — Megan Bowman

(57) ABSTRACT

A new and distinct cultivar of *Phlox* plant named 'Balcloudlue', characterized by its purple flowers with a dark purple center, medium, green-colored foliage, and moderately vigorous, compact-upright growth habit, is disclosed.

1 Drawing Sheet

Latin name of genus and species of plant claimed: *Phlox hybrida.*

Variety denomination: 'Balcloudlue'.

BACKGROUND OF THE INVENTION

The present invention relates to a new and distinct cultivar of *Phlox* plant botanically known as *Phlox hybrida* and hereinafter referred to by the cultivar name 'Balcloudlue'.

The new cultivar originated in a controlled breeding program in Hem, the Netherlands during the spring of 2017. The objective of the breeding program was the development of *Phlox* cultivars with attractive flower coloration, late-spring flowering and a moderately vigorous, mounded growth habit.

The new *Phlox* cultivar is the result of cross-pollination. The female (seed) parent of the new cultivar is the proprietary *Phlox amoena* breeding selection coded PHLP 478, not patented, characterized by its dark, purple-colored flowers, medium, green-colored foliage, and vigorous, mounded growth habit. The male (pollen) parent of the new cultivar is the proprietary *Phlox divaricata* ssp. *laphamii* breeding selection coded PHLP 491, not patented, characterized by its light purple-colored flowers, medium, green-colored foliage, and vigorous, mounded growth habit. The new cultivar was selected as a single flowering plant within the progeny of the above stated cross-pollination during April 2020 in a controlled environment in Hem, the Netherlands.

Asexual reproduction of the new cultivar by terminal stem cuttings since May 2017 in Hem, the Netherlands and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcloudlue' as a new and distinct cultivar of *Phlox* plant:

1. Purple flowers with a dark purple center;
2. Medium, green-colored foliage; and
3. Moderately vigorous, mounded growth habit.

Plants of the new cultivar differ from plants of the female and male parents primarily in having lighter, purple-colored flowers.

Of the many commercially available *Phlox* cultivars, the most similar in comparison to the new cultivar is Spring Splash Pink 'Balsashink', U.S. Plant Pat. No. 36,503. However, in side-by-side comparisons, plants of the new cultivar differ from plants of 'Balsashink' in at least the following characteristics:

1. Plants of the new cultivar have a more upright mounded habit than plants of 'Balsashink';
2. Plants of the new cultivar flowers earlier than plants of 'Balsashink'; and
3. Plants of the new cultivar have medium, blue-colored flowers unlike plants of 'Balsashink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcloudlue'. The plants were approximately nine months old. The plants were grown for approximately 24 weeks in an indoor greenhouse environment in Elburn, Illinois.

DETAILED BOTANICAL DESCRIPTION

Figure 1:
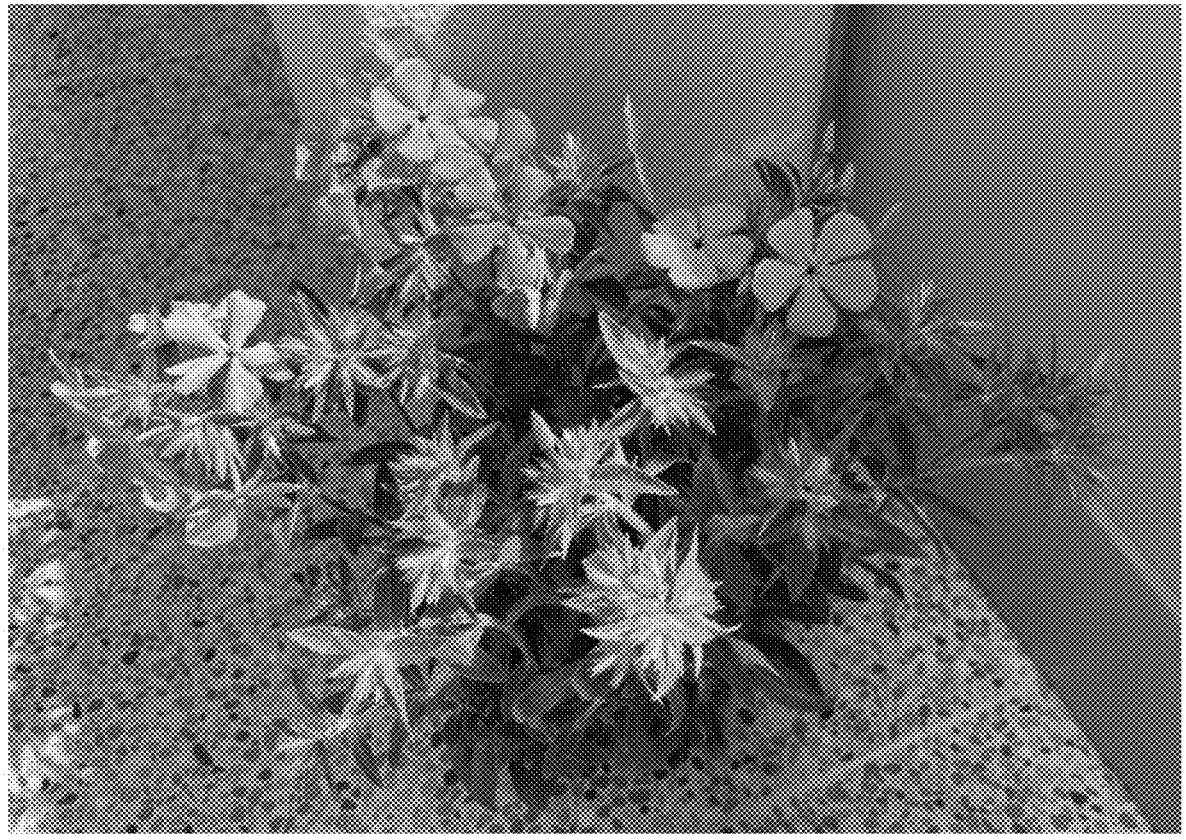
FIG. 1 illustrates a side view of the overall growth and flowering habit of 'Balcloudlue'.
Figure 2:
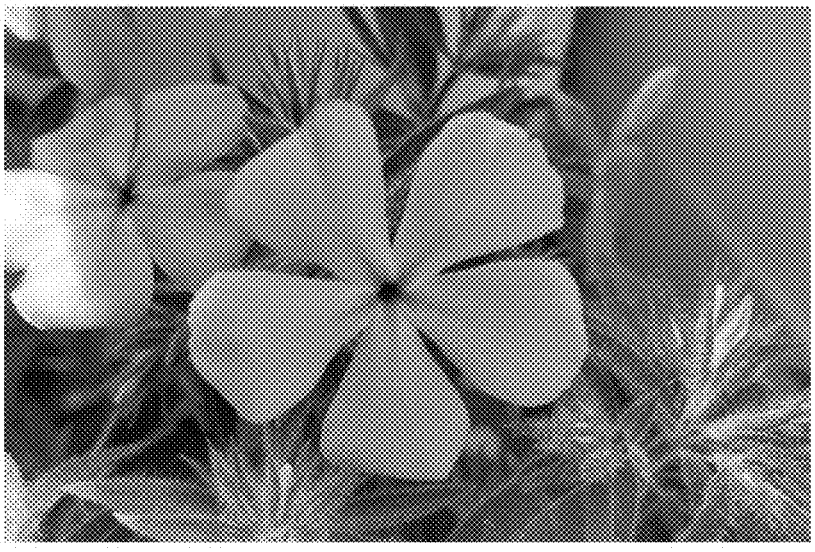
FIG. 2 illustrates a close-up view of an individual inflorescence of 'Balcloudlue'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2019 reprint of the 2015 edition, except where general color terms of ordinary significance are used. The color values were determined in March 2025 under natural light conditions in West Chicago, Illinois.

The following descriptions and measurements describe approximately nine-month-old plants produced from cuttings from stock plants and grown under conditions comparable to those used in commercial practice. Rooted cuttings were transplanted in one-gallon containers and grown in a poly-covered greenhouse in Elburn, Illinois. Plants were given two pinches five weeks and 11 weeks after transplant. After approximately 11 weeks, plants were then transplanted in an indoor greenhouse in Elburn, Illinois and grown for approximately 28 weeks. Greenhouse temperatures ranged from an average high of an average high of 45.0° F. (7.2° C.) to an average low of 40.0° F. (4.4° C.). No supplemental lighting was provided. Measurements and numerical values represent averages of typical plants.

Botanical classification: *Phlox hybrida* 'Balcloudlue'.

Parentage:

*Female parent*.—Proprietary *Phlox amoena* breeding selection coded PHLP 478, not patented.

*Male parent*.—Proprietary *Phlox divaricata* ssp. *laphamii* breeding selection coded PHLP 491, not patented.

Propagation:

*Type cutting*.—Terminal stem.

*Time to initiate roots*.—Approximately 10 to 12 days.

*Time to produce a rooted cutting*.—Approximately 42 to 49 days.

*Root description*.—Fine to medium thickness.

*Rooting habit*.—Freely branching, medium density.

Plant description:

*Commercial crop time*.—Approximately 10 to 12 weeks from a rooted cutting to finish in a 15 cm pot.

*Growth habit and general* appearance.—Herbaceous perennial, moderately vigorous, mounded growth habit.

*Hardiness*.—USDA Zone 4b (−25° F. to −20° F./−31.7° C. to −28.9° C.).

*Size*.—Height: Approximately 18 cm. Width: Approximately 29 cm.

*Branching habit*.—Freely branching, pinching will improve branching.

*Branch*.—Quantity: Approximately 6 basal branches. Shape: Round. Strength: Strong. Length to base of inflorescence: Approximately 21 cm. Diameter: Approximately 3 mm. Length of central internode: Approximately 3.0 cm. Slightly glossy with surface densely covered with short glandular hairs, an average of 0.5 mm in length. Color of young stems: 144B with an overlay of N79 towards the inflorescence. Color of mature stems: 146D, becoming woody 199B with age.

Foliage description:

*General description*.—Quantity of leaves per main branch: Approximately 16. Fragrance: None detected. Form: Simple. Arrangement: Opposite, decussate.

*Leaves*.—Shape: Lanceolate. Margin: Entire and ciliate. Apex: Acute. Base: Attenuate. Venation pattern: Pinnate. Length: Approximately 2.5 to 3.5cm. Width: Approximately 1.2 cm. Texture of upper surface: Sparsely pubescent. Texture of lower surface: Sparsely pubescent. Color of upper surface of young and mature foliage: Closest to 137B with venation of 136B. Color of lower surface of young and mature foliage: Closest to 137C with venation of 147B.

*Petioles*.—Length: Approximately 1.5 mm. Width: Approximately 2.0 mm: Glabrous. Color: 145C.

Flowering description:

*Flowering habit*.—'Balcloudlue' is a long day obligate and is freely flowering under outdoor growing conditions with substantially continuous blooming from late spring throughout summer.

*Lastingness of individual flower on the plant*.—Approximately 10 days.

Inflorescence description:

*General description*.—Type: Compound terminal panicle with clusters of salverform self-cleaning flowers. Quantity flowers per plant: Approximately 3 to 5. Fragrance: Moderately sweet and pleasant. Height of primary: Approximately 5.0 cm. Width of primary: Approximately 8.0 cm. Height of secondary: Approximately 4.0 cm. Width of secondary: 3.0 cm.

*Peduncle*.—Strength: Strong. Aspect: Primary erect, axillary acute angle to stem. Length of primary: Approximately 1.5 cm. Diameter of primary: Approximately 1.0 to 1.5 mm. Length of axillary: Approximately 2.0 cm to 4.0 cm. Diameter of axillary: Approximately 1.0 mm. Texture: Densely pubescent. Color: 146A with an overlay of N79A.

Flower description:

*Type*.—Single.

*Bud*.—Rate of opening: Generally, takes 3 to 4 days for bud to progress from first color to fully open flower.

*Bud just before opening*.—Shape: Oblanceolate. Length: Approximately 2.0 cm. Diameter: Approximately 3.0 mm. Color: Calyx of 145B with a central streak of 79C and petal portion of N88C.

*Corolla*.—Shape: Salverform. Diameter: Approximately 3.5 cm. Depth: Approximately 1.5 cm. Eye Color: Closest to N77A.

*Petals*.—Quantity: Approximately 4 to 5 in a single whorl, base fused into a narrow tube. Lobe shape: Obovate. Margin: Entire. Apex: Obtuse. Lobe length: Approximately 1.5 cm. Lobe width: Approximately 1.0 cm. Texture of upper and lower surfaces: Smooth, glabrous. Color of upper surface when first open: N87D to N87C with an orifice of 83A. Color of lower surface when first open: N88D. Color of upper surface when fully open: N82B to N82C with an orifice of 83A. Color of lower surface when fully open: N87D.

*Corolla tube*.—Length: Approximately 1.5 cm. Diameter at distal end: Approximately 3.0 mm. Diameter at proximal end: Approximately 1.5 mm. Texture of outer surface: Pubescent. Texture of inner surface: Smooth, glabrous. Color of inner surface: 79C with 145C at base. Color of outer surface: 79C with 154C at base.

*Calyx*.—Shape: Cupped. Length: Approximately 1.0 cm. Diameter: Approximately 5.0 mm.

*Sepals*.—Quantity per flower: 5, lower half fused. Shape: Lanceolate. Apex: Narrowly apiculate. Length: Approximately 8.0 mm. Width: Approximately 1.0 mm. Texture of outer surface: Sparsely pubescent. Texture of inner surface: Smooth, glabrous. Color of inner surface: 145B with tip and thin central streak on upper half of 137B. Color of outer surface: 145B.

*Pedicel*.—Strength: Strong, flexible. Aspect: Primary erect, axillary acute angle to peduncle. Length: Approximately 5.0 mm. Diameter: Approximately 1.5 mm. Texture: Densely pubescent. Color: 143C with a streak of N77B

*Reproductive organs*.—Androecium: Stamen quantity: 5 per flower, adnate to corolla tube. Stamen length: Approximately 1.0 cm. Filament length of free portion: Approximately 8.0 mm. Anther shape: Sagittate. Anther length: Approximately 2.0 mm. Anther color: 13D. Pollen amount: Abundant. Pollen color: 13A. Gynoecium: Pistil quantity: 1 per flower. Pistil length: Approximately 2.0 mm. Stigma shape: Cleft, three-parted. Stigma color: 145C. Style length: Approximately 1.5 mm. Style color: 145D. Ovary length: Approximately 1.0 mm. Ovary color: 141C.

Seed and fruit production: Neither seed nor fruit production has been observed.

Disease and pest resistance: Good resistance to *Golovinomyces magnicellulatus* has been observed.

What is claimed is:

1. A new and distinct cultivar of *Phlox* plant named 'Balcloudlue', substantially as herein illustrated and described.

* * * * *